United States Patent
Laroussi et al.

(10) Patent No.: US 8,460,283 B1
(45) Date of Patent: Jun. 11, 2013

(54) LOW TEMPERATURE PLASMA GENERATOR

(75) Inventors: Mounir Laroussi, Virginia Beach, VA (US); Julien Jarrige, Paris (FR)

(73) Assignee: Old Dominion University, Norfolk, VA (US)

(*) Notice: Subject to any disclaimer, the term of this patent is extended or adjusted under 35 U.S.C. 154(b) by 779 days.

(21) Appl. No.: 12/583,222

(22) Filed: Aug. 17, 2009

Related U.S. Application Data

(60) Provisional application No. 61/211,870, filed on Apr. 3, 2009.

(51) Int. Cl.
*A61B 18/08* (2006.01)

(52) U.S. Cl.
USPC ............. 606/34; 606/40; 606/49; 315/111.21

(58) Field of Classification Search
USPC ............................ 606/34, 40, 49; 315/111.21
See application file for complete search history.

(56) References Cited

U.S. PATENT DOCUMENTS

| | | | | |
|---|---|---|---|---|
| 4,088,926 A | * | 5/1978 | Fletcher et al. | 315/111.21 |
| 4,318,028 A | * | 3/1982 | Perel et al. | 315/111.81 |
| 4,593,397 A | * | 6/1986 | Proud et al. | 372/82 |
| 6,099,523 A | * | 8/2000 | Kim et al. | 606/40 |
| 6,124,675 A | * | 9/2000 | Bertrand et al. | 315/111.91 |
| 6,475,217 B1 | * | 11/2002 | Platt | 606/49 |
| 7,719,200 B2 | * | 5/2010 | Laroussi | 315/111.81 |
| 8,232,729 B2 | * | 7/2012 | Kitano et al. | 315/111.21 |
| 8,294,369 B1 | * | 10/2012 | Laroussi | 315/111.21 |
| 2004/0116918 A1 | * | 6/2004 | Konesky | 606/34 |
| 2005/0171528 A1 | * | 8/2005 | Sartor et al. | 606/41 |
| 2006/0028145 A1 | * | 2/2006 | Mohamed et al. | 315/111.21 |
| 2008/0017616 A1 | * | 1/2008 | Lee et al. | 219/121.48 |
| 2008/0262488 A1 | * | 10/2008 | Penny et al. | 606/28 |
| 2009/0121638 A1 | * | 5/2009 | Price et al. | 315/111.21 |
| 2010/0308730 A1 | * | 12/2010 | Mohamed et al. | 315/111.21 |
| 2012/0187841 A1 | * | 7/2012 | Kindel et al. | 315/111.21 |

* cited by examiner

*Primary Examiner* — Linda Dvorak
*Assistant Examiner* — Jocelyn D Ram
(74) *Attorney, Agent, or Firm* — Wooten & Shaddock, PLC

(57) ABSTRACT

A plasma generator having a dielectric body; a first end wall and a second end wall attached or coupled to each end of the dielectric body to define a cavity within the dielectric body, and wherein the second end wall includes at least one discharge aperture formed therein; at least one gas inlet formed proximate the first end of the dielectric body; at least one anode located within the cavity of the dielectric body, wherein the at least one anode includes at least one anode aperture; at least one hollow discharge nozzle associated with each discharge aperture, and extending from the second end wall to a nozzle aperture, such that when a generated plasma is produced, the generated plasma flows through each discharge aperture, each associated discharge nozzles, and each associated nozzle aperture; and at least one cathode formed at least substantially around a portion of each discharge nozzle.

9 Claims, 11 Drawing Sheets

LOW TEMPERATURE PLASMA GENERATOR

CROSS-REFERENCE TO RELATED APPLICATIONS

This nonprovisional patent application claims the benefit of U.S. Provisional Patent Application Ser. No. 61/211,870, filed Apr. 3, 2009 the disclosure of which is incorporated herein by reference.

BACKGROUND OF THE INVENTION

1. Field of the Invention

This invention is drawn generally to plasma generators. In particular, the present invention is drawn to plasma generators capable of producing a plasma plume or jet in open room air.

2. Description of Related Art

Non-thermal plasmas, or "cold plasmas", at or near atmospheric pressures have recently received increased attention because of their use in several emerging novel applications such as excimer light sources, the surface modification of polymers, the biological and chemical decontamination of media, and certain medical applications.

SUMMARY OF THE INVENTION

The present invention relates generally to plasma generators. In particular, the present invention is drawn to plasma generators capable of producing a plasma plume or jet in open room air.

This method is based on the use of a cold plasma jet, generated by a plasma generator capable of emitting a low temperature plasma plume, jet, or discharge in ambient air. In various exemplary, nonlimiting embodiments of the present invention, a plasma generator, as described in more detail herein, is utilized to produce the appropriate plasma plume, jet, or discharge.

Non-thermal plasmas, or "cold plasmas", at or near atmospheric pressures have recently received increased attention because of their use in several emerging novel applications such as excimer light sources, the surface modifications of polymers, the biological and chemical decontamination of media, and certain medical applications. Generating plasma in open room air adds the advantage of eliminating the need for an enclosure. Due to the abundant presence of oxygen, nitrogen, and moisture in air, reactive chemical species are produced. Additionally, since the whole process is carried out at atmospheric pressure, no costly and impractical vacuum equipment is necessary.

The plasma generator of this invention is capable of producing a relatively long plasma plume or jet in open room air. The generated plasma plume remains at room temperature and can be placed in contact with sensitive materials such as skin, flesh, paper, cloth, etc. without causing any damage. Another advantage of the plasma generator of this invention is its portability.

In various exemplary, non-limiting embodiments, the plasma generator, or "plasma generator", comprises a cylindrical dielectric tube with a hole at the end where the plasma plume exits. Thus, the plasma generator can be hand-held like a "pencil" and the generated plume can be applied to the sample under treatment.

In various exemplary embodiments, the plasma generator can be used in applications requiring localized and precise plasma-treatment of materials that cannot withstand the harsh treatment of wet chemicals, high temperatures, or mechanical pressure. The plasma generator provides a means for disinfection, sterilization, and/or precise cleaning of small surfaces, disinfection of skin or wounds, healing of wounds, coagulation of blood, inactivation of dental bacteria, whitening of teeth, disinfecting root canals, removing plaque, and the like. The medical field including dentistry is only one exemplary area of use of the plasma generator.

Accordingly, this invention provides a plasma generator, which can be used for sterilization, plasma-assisted wound healing, and/or cell detachment.

This invention separately provides a plasma generator, which can be used for inactivation of dental bacteria, cleaning of dental caries, and/or sterilization of dental tools.

This invention separately provides a plasma generator, which can be used for modification of surface properties (hydrophilic, oleophilic . . . ), for example, of materials such as polymers.

This invention separately provides a plasma generator, which is portable, scalable, environmentally safe, easy to use, and operates at a relatively low temperature.

This invention separately provides a plasma generator, which allows for the generation of a single cold plasma plume.

This invention separately provides a plasma generator, which allows for the generation of multiple cold plasma plumes simultaneously.

This invention separately provides a plasma generator, which generates one or more plasma plumes at room temperature.

This invention separately provides a plasma generator, which generates one or more plasma plumes that can be placed in contact with sensitive materials such as skin, flesh, paper, cloth, etc. without causing any damage.

This invention separately provides a plasma generator for the modification of surfaces to make them more or less wettable (i.e. hydrophilic, hydrophobic).

This invention separately provides a plasma generator, which may be portable.

This invention separately provides a plasma generator, which has a simplified design.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF THE PREFERRED EMBODIMENT

For simplicity and clarification, the design factors and operating principles of the plasma generator according to this invention are explained with reference to various exemplary embodiments of a plasma generator according to this invention. The basic explanation of the design factors and operating principles of the plasma generator is applicable for the understanding, design, and operation of the plasma generator of this invention.

Furthermore, it should be appreciated that, for simplicity and clarification, the embodiments of this invention will be described with reference to the plasma generator comprising circular dielectric disks and a cylindrical dielectric tube. However, it should be appreciated that the dielectric disks and dielectric tube or tubes of this invention may comprise circular, oval, rectangular, square, pentagonal, or any other geometric shapes.

It should also be appreciated that the term "plasma generator" is for basic explanation and understanding of the operation of the methods and/or apparatuses of this invention. Therefore, the term "plasma generator" is not to be construed as limiting the methods and/or apparatuses of this invention.

Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding both of those included limits are also included in the invention.

Figure 1A:
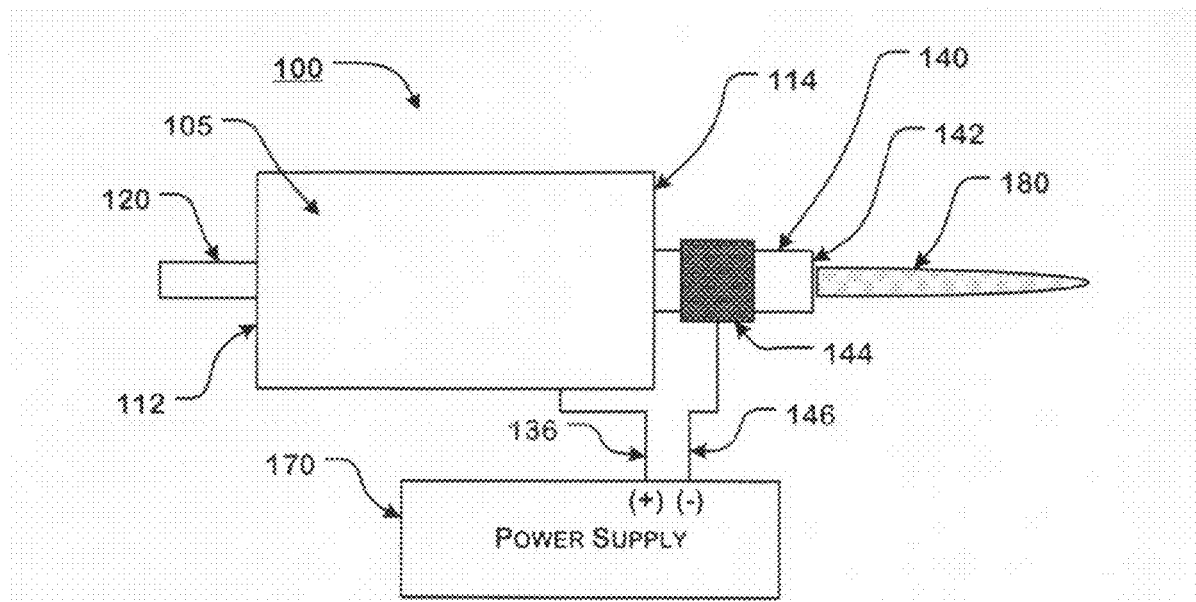
FIG. 1A shows a side view of a first illustrative, non-limiting embodiment of an exemplary plasma generator according to this invention.
Figure 1B:
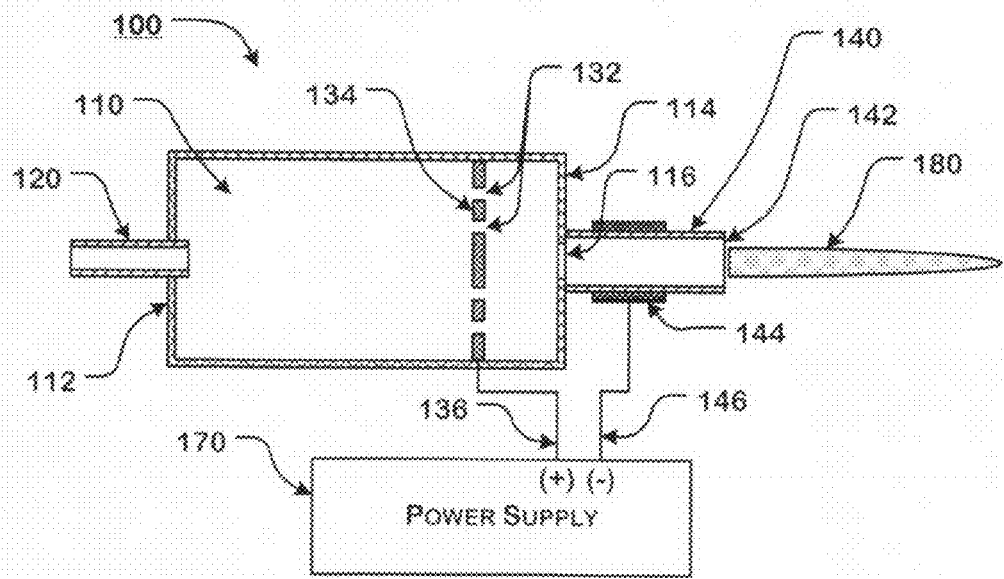
FIG. 1B shows a cross-sectional view of the first illustrative, non-limiting embodiment of an exemplary plasma generator according to this invention.

Turning now to FIGS. 1A and 1B, FIGS. 1A and 1B show a side and cross-sectional view, respectively, of a first illustrative, non-limiting embodiment of an exemplary plasma generator according to this invention. As illustrated in FIGS. 1A and 1B, the plasma generator 100 comprises a dielectric body 105 having a first end wall 112 and a second end wall 114 and defining a cavity 110.

One or more gas inlets 120 is/are located proximate the first end wall 112 of the dielectric body 105 and is/are in fluid communication with the cavity 110 of the plasma generator 100. The one or more gas inlet(s) 120 may be located at the first end wall 112 of the dielectric body 105 so as to allow gas to be introduced into the cavity 110 approximately parallel to a longitudinal axis of the plasma generator 100, as illustrated, for example, in FIGS. 1A and 1B. Alternatively, the one or more gas inlet(s) 120 may be located proximate the first end wall 112 so as to allow gas to be introduced into the cavity 110 and approximately perpendicular to the longitudinal axis of the plasma generator 100, as illustrated by gas inlet 720 illustrated, for example, in FIGS. 7A and 7B.

A discharge aperture 116 is formed through the second end wall 114. A hollow discharge nozzle 140 surrounds the discharge aperture 116 and extends from the second end wall 114 to a nozzle aperture 142. It should be appreciated that the size and shape of the discharge aperture 116 is a design choice based on the desired functionality of the plasma generator 100. Likewise, it should also be appreciated that the size, shape, length, and inner diameter of the discharge nozzle 140 are also a design choice based on the desired functionality of the plasma generator 100.

In various exemplary, non-limiting embodiments, the cavity 110 of the dielectric body 105 is hermetically sealed or closed, but for the gas inlet 120 and the discharge aperture 116.

At least one anode 134 is fitted or formed within or proximate the cavity 110 of the dielectric body 105. At least one cathode 144' is fitted or formed at least substantially around a portion of the discharge nozzle 140.

The anode 134 comprises an electrically conductive material, such as, for example, a metal, and includes one or more anode apertures 132 formed therethrough. The anode 134 is electrically coupled, via an electrical connection 136, to a power supply 170. In various exemplary embodiments, the end of anode 134 comprises a plate having one or more anode apertures 132 formed therethrough. Alternatively, the anode 134 may comprise a mesh or mesh-like formation of material wherein the anode apertures 132 are created by gaps between interwoven components of the anode 134.

The cathode 144 comprises an electrically conductive material, such as, for example, a metal. In various exemplary embodiments, the cathode 144 may be positioned external to the discharge nozzle 140 or may be embedded within the discharge nozzle 140. The cathode 144 is attached or coupled to or around the discharge nozzle 140 such that at least a portion of the discharge nozzle 140 isolates the cathode 144 from the interior of the discharge nozzle 140. Thus, any gas that flows through the discharge nozzle 140 is isolated from the cathode 144 such that the gas does not come into direct contact with the cathode 144.

The cathode 144 is electrically coupled, via an electrical connection 146, to the power supply 170.

In various exemplary, non-limiting embodiments, at least a portion of the dielectric body 105 and/or the discharge nozzle 140 may be formed of glass, Plexiglass, quartz, alumina, ceramic, or the like. The material that comprises the dielectric body 105 and discharge nozzle 140 may be the same material or may be a different material. It should also be appreciated that the dielectric body 105 and/or the discharge nozzle 140 may be formed of multiple materials. Thus, it should be understood that the material or materials used to form the dielectric body 105 and/or the discharge nozzle 140 is a design choice based on the desired appearance, strength, and functionality of the plasma generator 100.

In various exemplary, non-limiting embodiments, the distance that separates the anode 134 from the cathode 144 is approximately 1-40 mm.

Utilizing the plasma generator 100, a carrier gas (or mixture) is introduced proximate the first end wall 112 of the dielectric body 105, via the one or more gas inlet(s) 120. In various exemplary embodiments, the carrier gas (or mixture) is injected into the plasma generator at a flow rate of approximately 1-10 l/min. In various exemplary, non-limiting embodiments, the gas or gas mixtures may comprise helium, a helium and oxygen mixture, argon, nitrogen, air, or other noble gases and/or their mixtures.

As the carrier gas (or mixture) is injected into the one or more gas inlet(s) 120, the gas flows through the cavity 110 of the dielectric body 105, through the anode aperture(s) 132 of the anode 134, through the discharge aperture 116, through the interior of the discharge nozzle 140, and exits through the nozzle aperture 142 of the discharge nozzle 140.

When power is applied to the anode 134 and the cathode 144, the injected gas breaks down and a plasma plume 180 is launched through the nozzle aperture 142 of the discharge nozzle 140. The generated plasma plume 180 generally extends from the plasma generator 100 in a direction that is substantially parallel to the longitudinal axis of the discharge nozzle 140. The generated plasma plume 180 is at room temperature and remains stable so long as the carrier gas is flowing and an appropriate amount of power is applied to the anode 134 and the cathode 144.

In various exemplary, non-limiting embodiments, the power supply 170 can supply Alternating Current (AC), Radio Frequency (RF) power, or regulated voltage pulses of varying widths and of varying frequencies to the anode 134 and the cathode 144. In certain embodiments, the plasma generator 100 is driven by nanosecond/microsecond voltage pulses to, in turn, produce nanosecond/microsecond plasma plumes.

The power supply 170 may optionally supply the plasma generator 100 with a pulsed voltage having a magnitude from 2 kilovolts to 12 kilovolts, applied at a pulse width of between 200 nanoseconds to 5 microseconds, and/or applied at a frequency of 1 kilohertz to 10 kilohertz or higher.

In various exemplary, non-limiting embodiments, the power supply 170 supplies between 1-20 watts of power to the anode 134 and the cathode 144. It should be understood that, in various exemplary embodiments, the power supply 170 may supply up to several hundred watts of power to the anode 134 and the cathode 144. It should be appreciated that the frequency and amount of power supplied by the power supply 170 may be altered to produce a generated plasma plume 180 having a desired strength, functionality, size, and/or duration.

In various exemplary embodiments, the plasma plume 180 may measure 2 inches or more, while the width of the plasma plume 180 is generally determined by the diameter or size of the discharge aperture 116 and/or nozzle aperture 142. In various exemplary embodiments, the diameter of the nozzle aperture 142 may be approximately a few millimeters to about 1 centimeter.

Figure 2A:
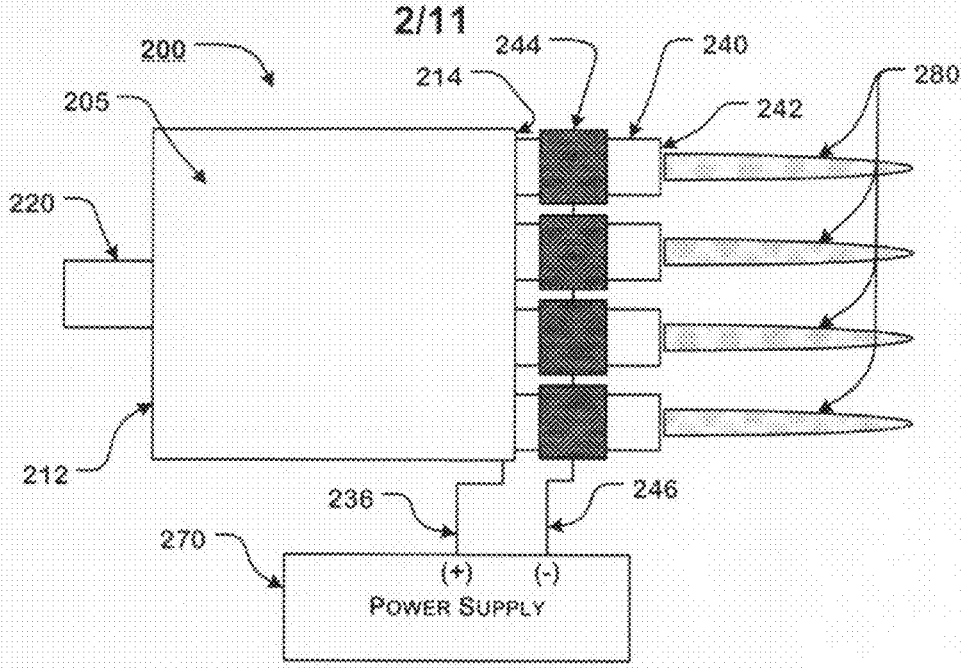
FIG. 2A shows a side view of a second illustrative, non-limiting embodiment of an exemplary plasma generator according to this invention.
Figure 2B:
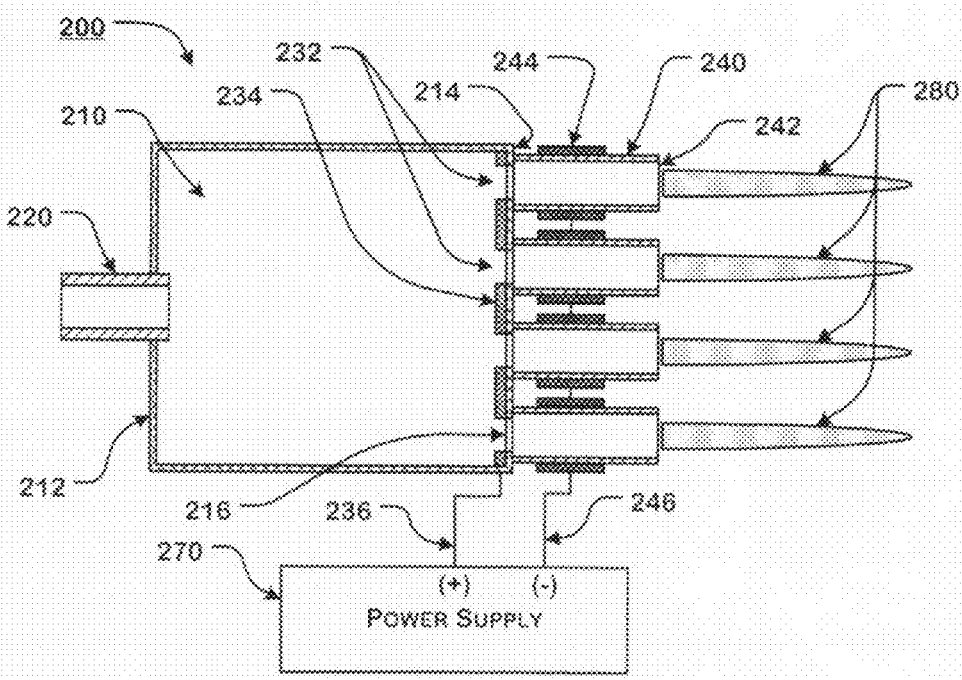
FIG. 2B shows a cross-sectional view of the second illustrative, non-limiting embodiment of an exemplary plasma generator according to this invention.

FIGS. 2A and 2B show a side view and a cross-sectional view, respectively, of a second illustrative, non-limiting embodiment of an exemplary plasma generator according to this invention. As illustrated in FIGS. 2A and 2B, the plasma generator 200 comprises a dielectric body 205 having a first end wall 212, a second end wall 214, a cavity 210, one or more gas inlet(s) 220, and at least one anode 234 having one or more anode apertures 232 formed therethrough, an electrical connection 236, an electrical connection 246, and a power supply 270.

It should be understood that each of these elements, if included, corresponds to and operates similarly to the dielectric body 105, the first end wall 112, the second end wall 114, the cavity 110, the one or more gas inlet(s) 120, the at least one anode 134 having one or more anode apertures 132 formed therethrough, the electrical connection 136, the electrical connection 146, and the power supply 170, as described above with reference to the plasma generator 100 of FIG. 1.

However, as illustrated in FIGS. 2A and 2B, the plasma generator 200 comprises a plurality of discharge apertures 216, each having an associated hollow discharge nozzle 240 that surrounds its associated discharge aperture 216 and extends, substantially parallel to the longitudinal axis of the plasma generator 200, from the second end wall 214 to a nozzle aperture 242. At least one cathode 244 is fitted or formed at least substantially around a portion of each discharge nozzle 240. An electrical connection 246 electrically couples each cathode 244 to the power supply 270.

The anode 234 is attached or coupled proximate the second end wall 214 such that each anode aperture 232 surrounds an associated discharge aperture 216.

During use of the plasma generator 200, a carrier gas (or mixture) is introduced proximate the first end wall 212 of the dielectric body 205, via the one or more gas inlet(s) 220, as described above, with respect to FIGS. 1A and 1B.

As the carrier gas (or mixture) is injected into the one or more gas inlet(s) 220, the gas flows through the cavity 210 of the dielectric body 205, through the anode apertures 232 of the anode 234, through the discharge apertures 216, through the interior of the discharge nozzles 240, and exits through the nozzle apertures 242 of the discharge nozzles 240.

When power is applied to the anode 234 and the cathodes 244, the injected gas breaks down and a plasma plume 280 is launched through each of the nozzle apertures 242 of the discharge nozzles 240. The generated plasma plumes 280 generally extend from the plasma generator 200 in a direction that is substantially parallel to the longitudinal axis of the discharge nozzles 240. The generated plasma plumes 280 are at room temperature and remain stable so long as the carrier gas is flowing and an appropriate amount of power is applied to the anode 234 and the cathodes 244.

Figure 3A:
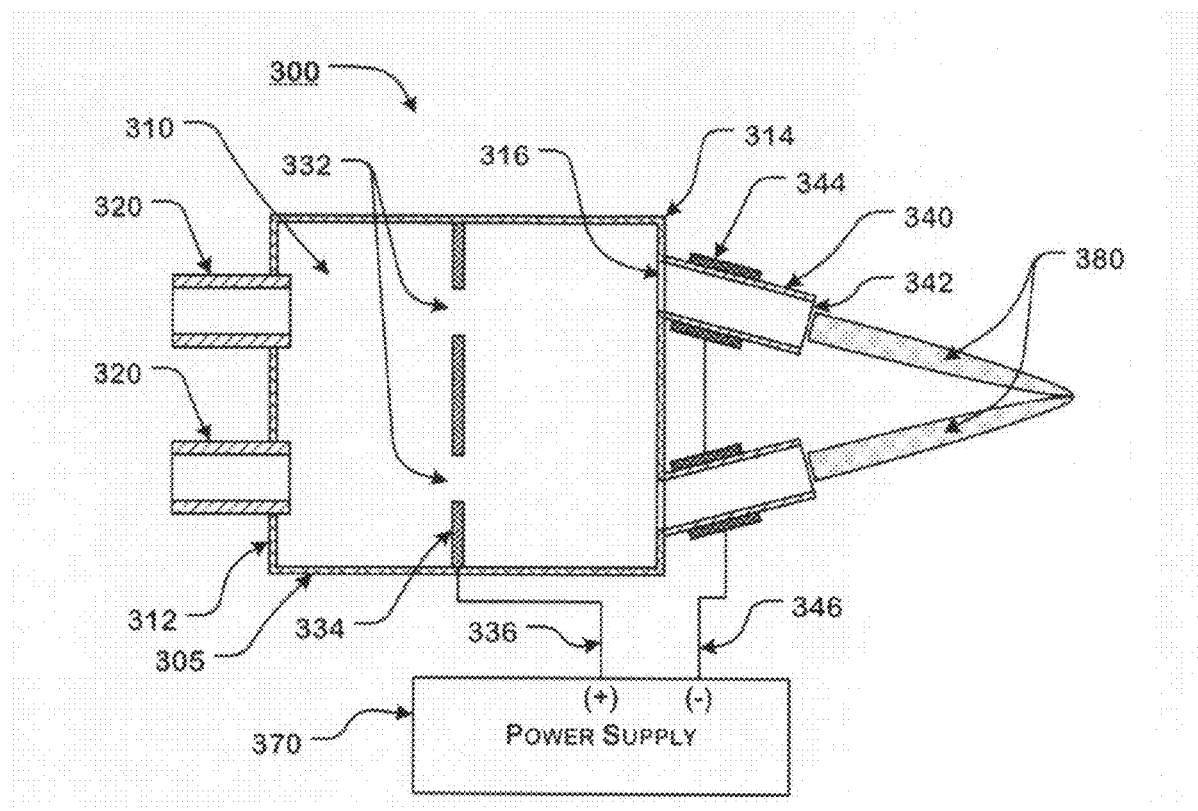
FIG. 3A shows a cross-sectional view of a third illustrative, non-limiting embodiment of an exemplary plasma generator according to this invention.
Figure 3B:
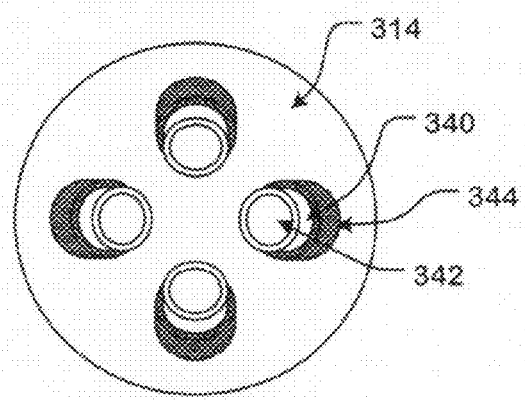
FIG. 3B shows a front view of the third illustrative, non-limiting embodiment of an exemplary plasma generator according to this invention.

FIGS. 3A and 3B show a cross-sectional view and a front view, respectively, of a third illustrative, non-limiting embodiment of an exemplary plasma generator according to this invention. As illustrated in FIGS. 3A and 3B, the plasma generator 300 comprises a dielectric body 305 having a first end wall 312, a second end wall 314, a cavity 310, one or more gas inlet(s) 320, a plurality of discharge apertures 316, each with an associated hollow discharge nozzle 340 having a nozzle aperture 342, a cathode 344 fitted or formed at least substantially around a portion of each discharge nozzle 340, and at least one anode 334 having one or more anode apertures 332 formed therethrough, an electrical connection 336 electrically coupling the anode 334 to a power supply 370, and an electrical connection 346 electrically coupling each cathode 344 to the power supply 370.

It should be understood that each of these elements, if included, corresponds to and operates similarly to the dielectric body 205, the first end wall 212, the second end wall 214, the cavity 210, the one or more gas inlet(s) 220, the plurality of discharge apertures 216, the hollow discharge nozzles 240, the nozzle apertures 242, the cathodes 244, the at least one anode 234 having one or more anode apertures 232 formed therethrough, the electrical connection 236, the electrical connections 246, and the power supply 270, as described above with reference to the plasma generator 200 of FIG. 2.

However, as illustrated in FIGS. 3A and 3B, the discharge nozzles 340 are arranged in a substantially circular pattern and extend from the second end wall 314 such that when generated plasma plumes 380 are generated, the generated plasma plumes 380 effectively converge at a point in space. It should be appreciated that the discharge nozzles 340 may be placed at any desired angle such that the generated plasma plumes 380 converge at a desired point or such that the generated plasma plumes 380 are angled towards one another at a desired angle.

Optionally, the anode 334 may optionally be attached or coupled within the cavity 310, as opposed to being located proximate the second end wall 314 (as the anode 234, illustrated in FIG. 2B).

Figure 4A:
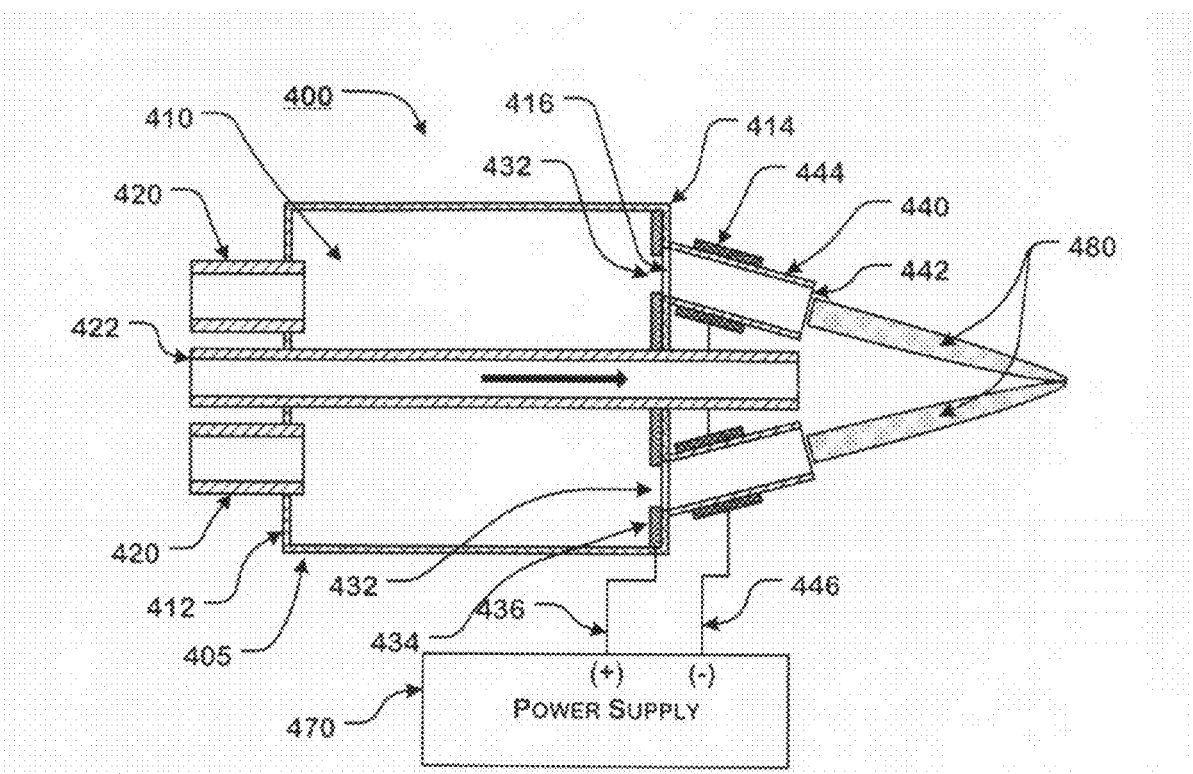
FIG. 4A shows a cross-sectional view of a fourth illustrative, non-limiting embodiment of an exemplary plasma generator according to this invention.
Figure 4B:
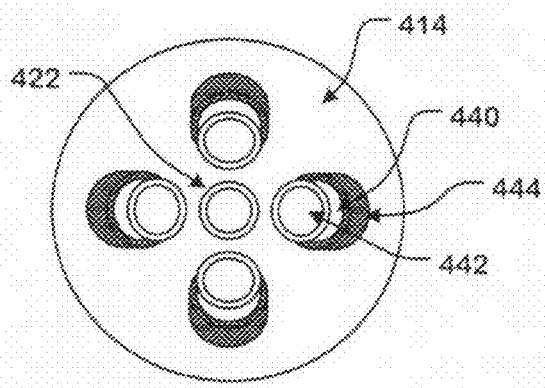
FIG. 4B shows a front view of the fourth illustrative, non-limiting embodiment of an exemplary plasma generator according to this invention.

FIGS. 4A and 4B show a cross-sectional view and a front view, respectively, of a fourth illustrative, non-limiting embodiment of an exemplary plasma generator according to this invention. As illustrated in FIGS. 4A and 4B, the plasma generator 400 comprises a dielectric body 405 having a first end wall 412, a second end wall 414, a cavity 410, one or more gas inlet(s) 420, a plurality of discharge apertures 416, each with an associated hollow discharge nozzle 440 having a nozzle aperture 442, a cathode 444 fitted or formed at least substantially around a portion of each discharge nozzle 440, and at least one anode 434 having one or more anode apertures 432 formed therethrough, an electrical connection 436 electrically coupling the anode 434 to a power supply 470, and an electrical connection 446 electrically coupling each cathode 444 to the power supply 470.

It should be understood that each of these elements, if included, corresponds to and operates similarly to the dielectric body 305, the first end wall 312, the second end wall 314, the cavity 310, the one or more gas inlet(s) 320, the plurality of discharge apertures 316, the hollow discharge nozzles 340, the nozzle apertures 342, the cathodes 344, the at least one anode 334 having one or more anode apertures 332 formed therethrough, the electrical connection 336, the electrical connections 346, and the power supply 370, as described above with reference to the plasma generator 300 of FIG. 3.

However, as illustrated in FIGS. 4A and 4B, an additional gas inlet tube 422 is included. The additional gas inlet tube 422 allows an additional stream of gas, fluid, or chemical additives to flow through the plasma generator 400 in order to enhance, spread, or otherwise alter the generated plasma plumes 480. It should be appreciated that while the outlet of the additional gas inlet tube 422 is illustrated as being substantially circular, the outlet of the additional gas inlet tube 422 may be shaped or formed so as to alter the generated plasma plumes in a desired manner.

Figure 5A:
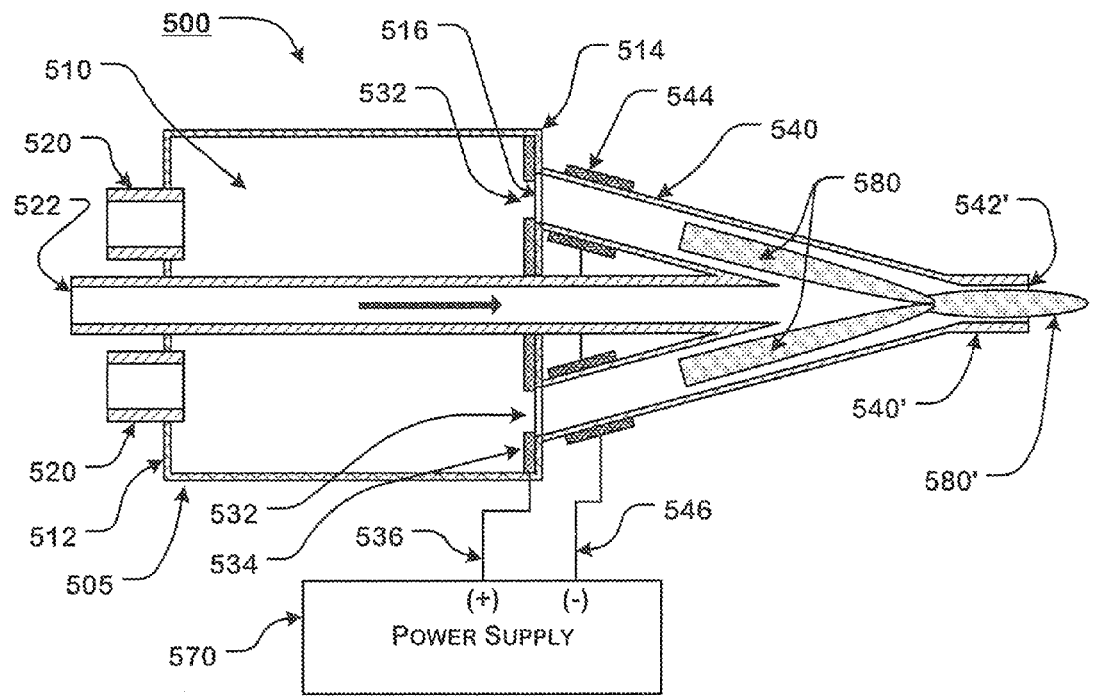
FIG. 5A shows a cross-sectional view of a fifth illustrative, non-limiting embodiment of an exemplary plasma generator according to this invention.
Figure 5B:
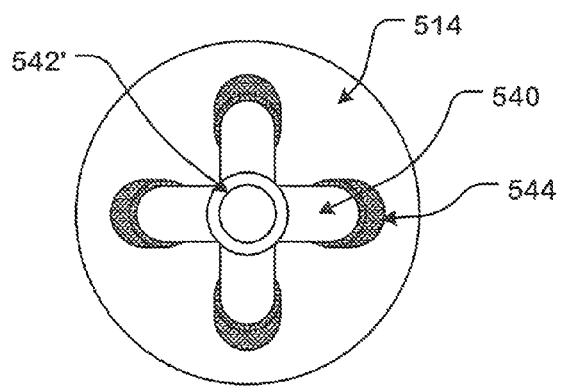
FIG. 5B shows a front view of the fifth illustrative, non-limiting embodiment of an exemplary plasma generator according to this invention.

FIGS. 5A and 5B show a cross-sectional view and a front view, respectively, of a fifth illustrative, non-limiting embodiment of an exemplary plasma generator according to this invention. As illustrated in FIGS. 5A and 5B, the plasma generator 500 comprises a dielectric body 505 having a first end wall 512, a second end wall 514, a cavity 510, a plurality of discharge apertures 516, each with an associated hollow discharge nozzle 540 having a nozzle aperture, one or more gas inlet(s) 520, an additional gas inlet tube 522, a cathode 544 fitted or formed at least substantially around a portion of each discharge nozzle 540, and at least one anode 534 having one or more anode apertures 532 formed therethrough, an electrical connection 536 electrically coupling the anode 534 to a power supply 570, and an electrical connection 546 electrically coupling each cathode 544 to the power supply 570.

It should be understood that each of these elements, if included, corresponds to and operates similarly to the dielectric body 405, the first end wall 412, the second end wall 414, the cavity 410, the plurality of discharge apertures 416, the one or more gas inlet(s) 420, the additional gas inlet tube 422, the hollow discharge nozzles 440, the nozzle apertures 442, the cathodes 444, the at least one anode 434 having one or more anode apertures 432 formed therethrough, the electrical connection 436, the electrical connections 446, and the power supply 470, as described above with reference to the plasma generator 400 of FIGS. 4A and 4B.

However, as illustrated in FIGS. 5A and 5B, the additional gas inlet tube 522 and the hollow discharge nozzles 540 are extended so as to converge with one another. The convergent additional gas inlet tube 522 and hollow discharge nozzles 540 join to form a terminal discharging pipe 540' having a nozzle aperture 542'.

The convergence of the additional gas inlet tube 522 and the hollow discharge nozzles 540 to form the terminal discharging pipe 540' allows additional control and isolation of the stream of gas or fluid that flow through the plasma generator 500 in order to enhance, spread, or otherwise alter the convergent plasma plumes 580 and the resultant plasma plume 580'. It should be appreciated that while the nozzle aperture 542' of the terminal discharging pipe 540' is illustrated as being substantially circular, the nozzle aperture 542' may be shaped or formed so as to alter the resultant plasma plume 580' in a desired manner.

Figure 6A:
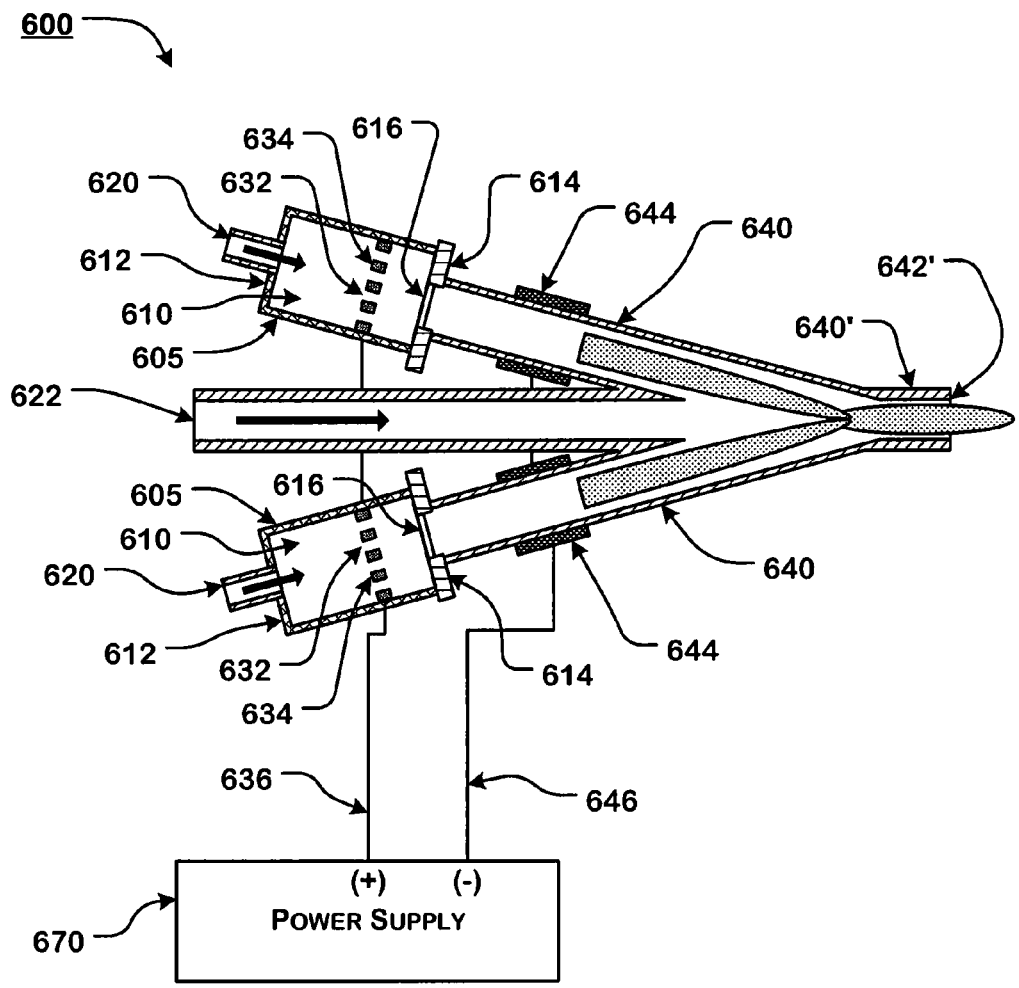
FIG. 6A shows a cross-sectional view of a sixth illustrative, non-limiting embodiment of an exemplary plasma generator according to this invention.
Figure 6B:
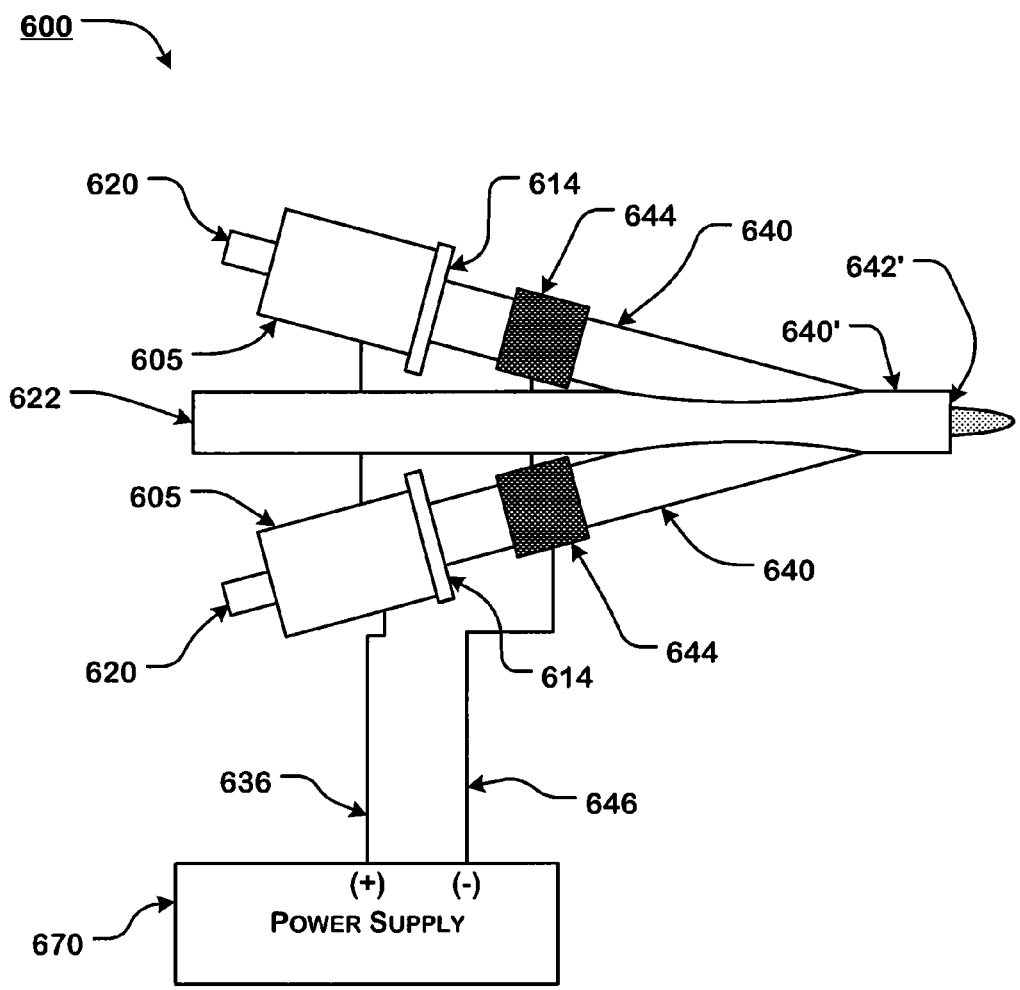
FIG. 6B shows a side view of the sixth illustrative, non-limiting embodiment of an exemplary plasma generator according to this invention.

FIGS. 6A and 6B show a cross-sectional view and a side view, respectively, of a sixth illustrative, non-limiting embodiment of an exemplary plasma generator according to this invention. As illustrated in FIGS. 6A and 6B, the plasma generator 600 comprises an additional gas inlet tube 622 and the hollow discharge nozzles 640 that are extended so as to converge with one another. The convergent additional gas inlet tube 622 and hollow discharge nozzles 640 join to form a terminal discharging pipe 640' having a nozzle aperture 642'. In this manner, the plasma generator 600 operates similarly to and has similar advantages to the plasma generator 500 of FIGS. 5A and 5B.

However, as illustrated in FIGS. 6A and 6B, each of the discharge nozzles 640 includes a dielectric body 605 having a first end wall 612, a second end wall 614, a cavity 610, a discharge aperture 616 that feeds into the hollow discharge nozzle 640, a cathode 644 fitted or formed at least substantially around a portion of each discharge nozzle 640, one or more gas inlet(s) 620, and at least one anode 634 having one or more anode apertures 632 formed therethrough, an electrical connection 636, and an electrical connection 646 electrically coupling each cathode 644 to the power supply 670.

It should be understood that each of these elements, if included, corresponds to and operates similarly to the dielectric body 105, the first end wall 112, the second end wall 114, the cavity 110, the discharge aperture 116, the one or more gas inlet(s) 120, the at least one anode 134 having one or more anode apertures 132 formed therethrough, the electrical connection 136, the electrical connection 146, and the power supply 170, as described above with reference to the plasma generator 100 of FIG. 1.

Figure 7A:
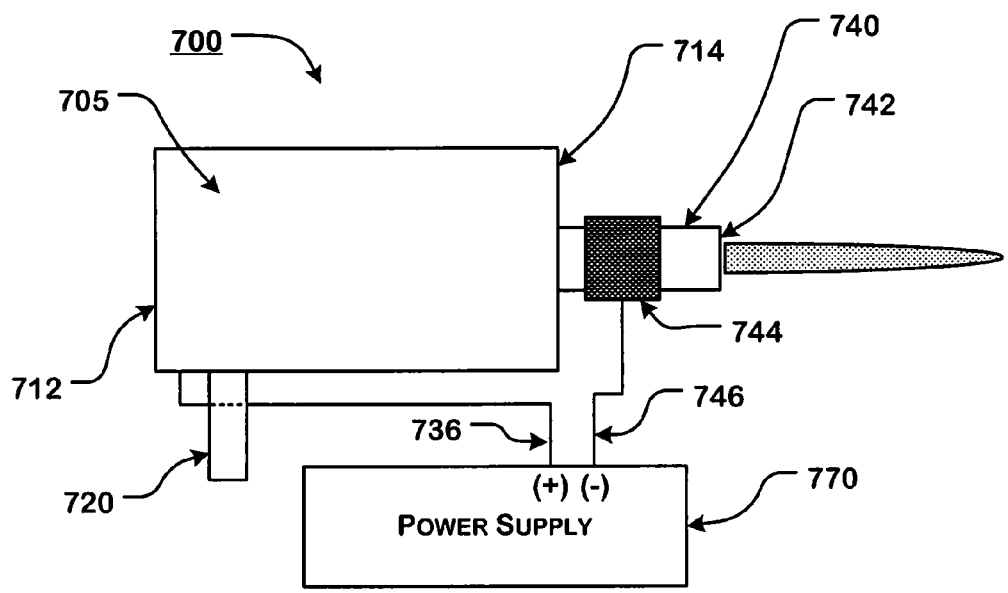
FIG. 7A shows a side view of a seventh illustrative, non-limiting embodiment of an exemplary plasma generator according to this invention.
Figure 7B:
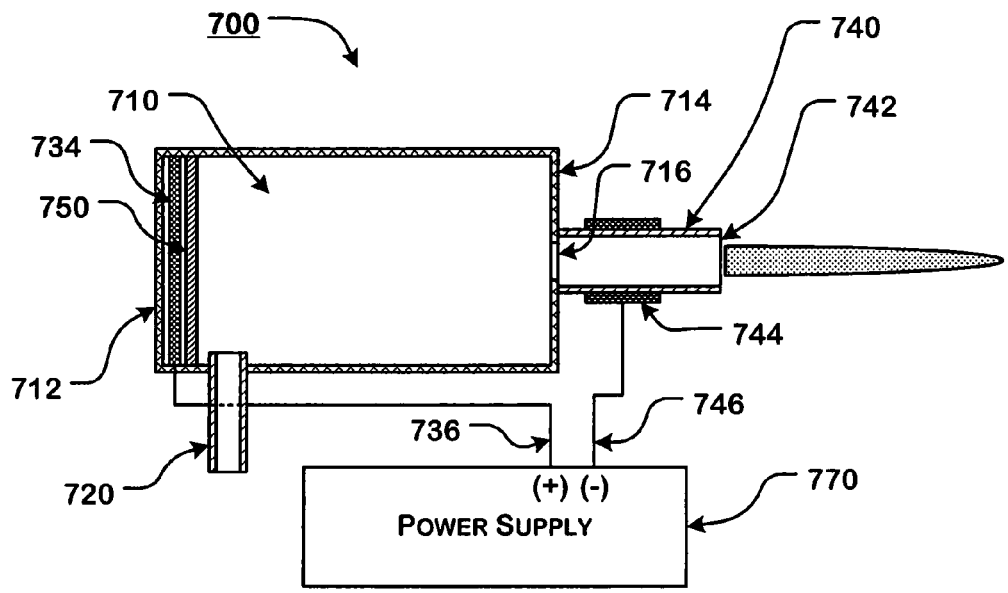
FIG. 7B shows a cross-sectional view of the seventh illustrative, non-limiting embodiment of an exemplary plasma generator according to this invention.

FIGS. 7A and 7B show a side view and a cross-sectional view, respectively, of a seventh illustrative, non-limiting embodiment of an exemplary plasma generator according to this invention. As illustrated in FIGS. 7A and 7B, the plasma generator 700 comprises a dielectric body 705 having a first end wall 712, a second end wall 714, a cavity 710, one or more gas inlet(s) 720, a discharge aperture 716, a hollow discharge nozzle 740 having a nozzle aperture 742, a cathode 744 fitted or formed at least substantially around a portion of the discharge nozzle 740, and at least one anode 734, an electrical connection 736 electrically coupling the anode 734 to a power supply 770, and an electrical connection 746 electrically coupling the cathode 744 to the power supply 770.

It should be understood that each of these elements, if included, corresponds to and operates similarly to the dielectric body 105, the first end wall 112, the second end wall 114, the cavity 110, the one or more gas inlet(s) 120, the discharge aperture 116, the hollow discharge nozzle 140, the cathode 144 fitted or formed at least substantially around a portion of the discharge nozzle 140, the at least one anode 134 having one or more anode apertures 132 formed therethrough, the electrical connection 136 electrically coupling the anode 134 to the power supply 170, and the electrical connection 146 electrically coupling the cathode 144 to the power supply 170, as described above with reference to the plasma generator 100 of FIG. 1.

However, as illustrated in FIGS. 7A and 7B, the one or more gas inlet(s) 720 is illustrated as being approximately perpendicular to the longitudinal axis of the plasma generator 700.

Additionally, a dielectric plate 750 is attached or coupled within a cavity 710 such that the anode 734 is isolated from any gas within the chamber 710. Thus, during the use of the plasma generator 700, any gas that flows through the chamber 710 is isolated from the anode 734 such that the gas does not come into direct contact with the anode 734.

Figure 8A:
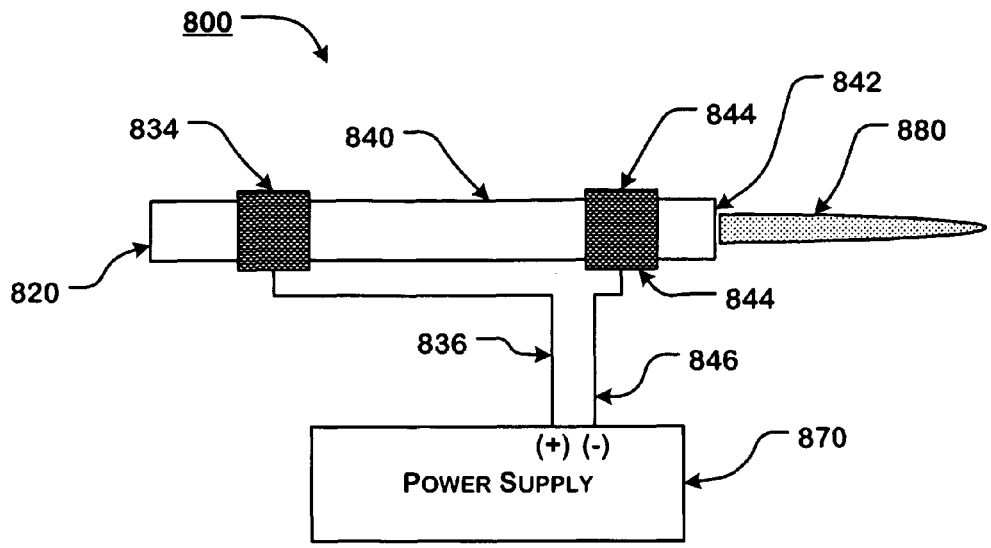
FIG. 8A shows a side view of a eighth illustrative, non-limiting embodiment of an exemplary plasma generator according to this invention.
Figure 8B:
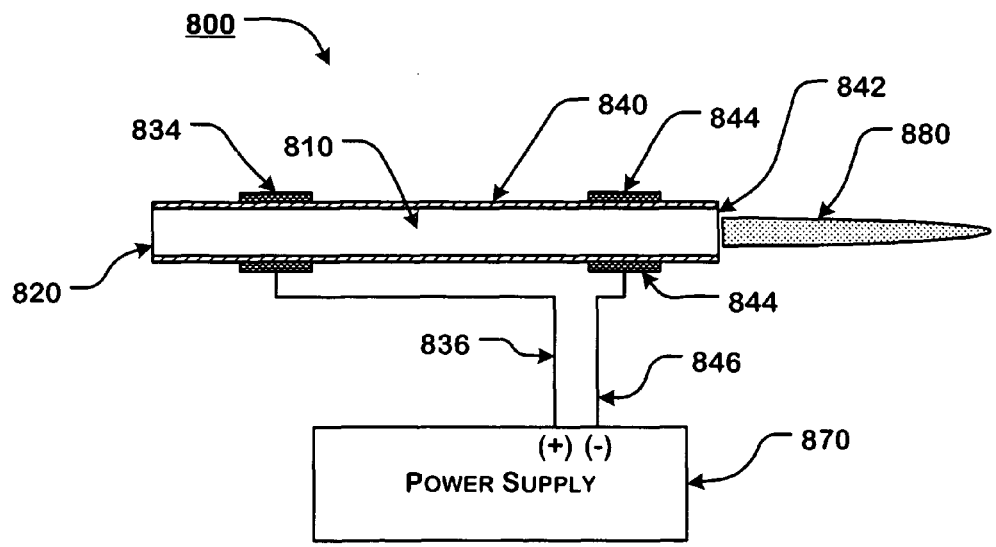
FIG. 8B shows a cross-sectional view of the eighth illustrative, non-limiting embodiment of an exemplary plasma generator according to this invention.

FIGS. 8A and 8B show a side and cross-sectional view, respectively, of a eighth illustrative, non-limiting embodiment of an exemplary plasma generator according to this invention. As illustrated in FIGS. 8A and 8B, the plasma generator 800 comprises a discharge nozzle 840 extending from a gas inlet 820, through a cavity 810, to a nozzle aperture 842.

It should also be appreciated that the size, shape, length, and inner diameter of the discharge nozzle 840 is a design choice based on the desired functionality of the plasma generator 800.

At least one anode 834 is attached or coupled to or around the discharge nozzle 840 such that at least a portion of the discharge nozzle 840 isolates the anode 834 from the interior of the discharge nozzle 840. Thus, any gas that flows through the discharge nozzle 840 is isolated from the anode 834 such that the gas does not come into direct contact with the anode 834.

The anode 834 comprises an electrically conductive material, such as, for example, a metal. In various exemplary embodiments, the anode 834 may be positioned external to the discharge nozzle 840 or may be embedded within the discharge nozzle 840. The anode 834 is electrically coupled, via an electrical connection 836, to the power supply 870.

At least one cathode 844 is attached or coupled to or around the discharge nozzle 840, spaced apart from the at least one anode 834 so as to avoid arcing between the cathode 844 and the anode 834. In various exemplary embodiments, an isolating material may be positioned between the cathode 844 and the anode 834 so as to provide electrical insulation between the cathode 844 and the anode 834.

At least a portion of the discharge nozzle 840 isolates the cathode 844 from the interior of the discharge nozzle 840. Thus, any gas that flows through the discharge nozzle 840 is isolated from the cathode 844 such that the gas does not come into direct contact with the cathode 844.

The cathode 844 comprises an electrically conductive material, such as, for example, a metal. In various exemplary embodiments, the cathode 844 may be positioned external to the discharge nozzle 840 or may be embedded within the discharge nozzle 840. The cathode 844 is electrically coupled, via an electrical connection 846, to the power supply 870.

In various exemplary, non-limiting embodiments, at least a portion of the discharge nozzle 840 may be formed of glass, Plexiglass, quartz, alumina, ceramic, or the like.

In various exemplary, non-limiting embodiments, the distance that separates the anode 834 from the cathode 844 is approximately 1-40 mm.

Utilizing the plasma generator 800, a carrier gas (or mixture) is injected into the gas inlet 820. In various exemplary embodiments, the carrier gas (or mixture) is injected into the plasma generator 800 at a flow rate of approximately 1-10 l/min. In various exemplary, non-limiting embodiments, the gas or gas mixtures may comprise helium, a helium and oxygen mixture, argon, nitrogen, air, or other noble gases and/or their mixtures.

As the carrier gas (or mixture) is injected into the gas inlet 820, the gas flows through the cavity 810 of the discharge nozzle 840 and exits through the nozzle aperture 842 of the discharge nozzle 840.

When power is applied to the anode 834 and the cathode 844, the injected gas breaks down and a plasma plume 880 is launched through the nozzle aperture 842 of the discharge nozzle 840. The generated plasma plume 880 generally extends from the plasma generator 800 in a direction that is substantially parallel to the longitudinal axis of the discharge nozzle 840. The generated plasma plume 880 is at room temperature and remains stable so long as the carrier gas is flowing and an appropriate amount of power is applied to the anode 834 and the cathode 844.

In various exemplary, non-limiting embodiments, the power supply 870 can supply Alternating Current (AC), Radio Frequency (RF) power, or regulated voltage pulses of varying widths and of varying frequencies to the anode 834 and the cathode 844. In certain embodiments, the plasma generator 800 is driven by nanosecond/microsecond voltage pulses to, in turn, produce nanosecond/microsecond plasma plumes.

The power supply 870 may optionally supply the plasma generator 800 with a pulsed voltage having a magnitude from 2 kilovolts to 12 kilovolts, applied at a pulse width of between 200 nanoseconds to 5 microseconds, and/or applied at a frequency of 1 kilohertz to 10 kilohertz or higher.

In various exemplary, non-limiting embodiments, the power supply 870 supplies between 1-20 watts of power to the anode 834 and the cathode 844. It should be understood that, in various exemplary embodiments, the power supply 870 may supply up to several hundred watts of power to the anode 834 and the cathode 844. It should be appreciated that the frequency and amount of power supplied by the power supply 870 may be altered to produce a generated plasma plume 880 having a desired strength, functionality, size, and/or duration.

Figure 9A:
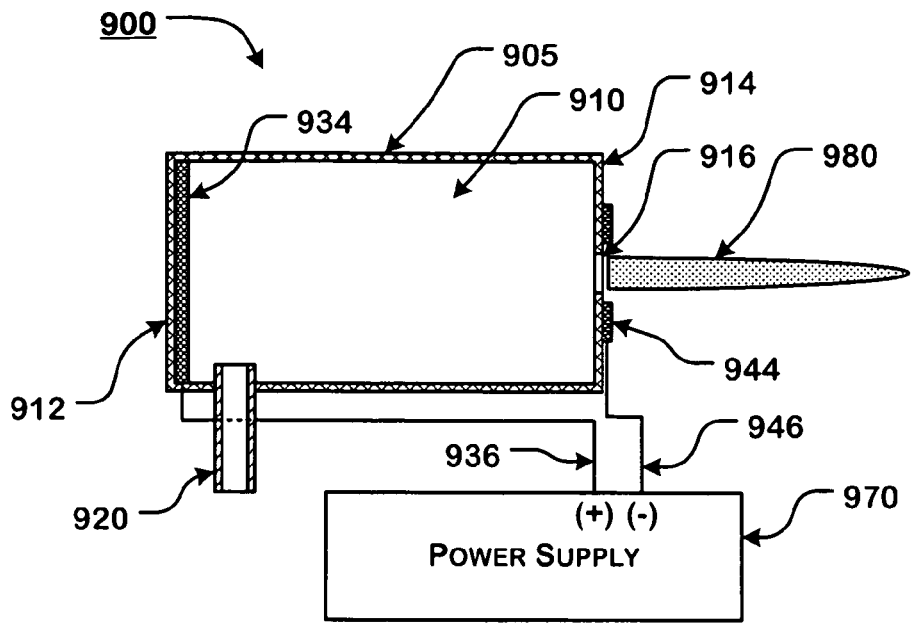
FIG. 9A shows a cross-sectional view of a ninth illustrative, non-limiting embodiment of an exemplary plasma generator according to this invention.
Figure 9B:
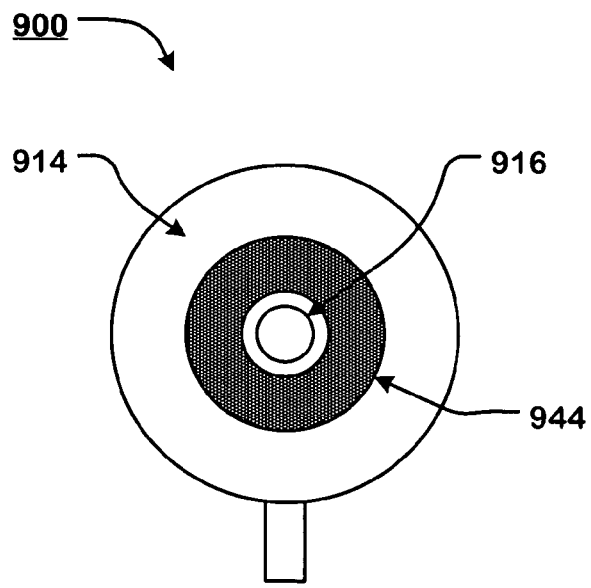
FIG. 9B shows a front view of the ninth illustrative, non-limiting embodiment of an exemplary plasma generator according to this invention.

FIGS. 9A and 9B show a cross-sectional view and a front view, respectively, of a ninth illustrative, non-limiting embodiment of an exemplary plasma generator according to this invention. As illustrated in FIGS. 9A and 9B, the plasma generator 900 comprises a dielectric body 905 having a first end wall 912 and a second end wall 914 and defining a cavity 910.

One or more gas inlets 920 is/are located proximate the first end wall 912 of the dielectric body 905 and is/are in fluid communication with the cavity 910 of the plasma generator 900. The one or more gas inlet(s) 920 may be located proximate the first end wall 912 so as to allow gas to be introduced into the cavity 900 and approximately perpendicular to the longitudinal axis of the plasma generator 900, as illustrated in FIGS. 9A and 9B. Alternatively, the one or more gas inlet(s) 920 may be located at the first end wall 912 of the dielectric body 905 so as to allow gas to be introduced into the cavity 910 approximately parallel to a longitudinal axis of the plasma generator 900, as illustrated, for example, in FIGS. 1A and 1B.

A discharge aperture 916 is formed through the second end wall 914. It should be appreciated that the size and shape of the discharge aperture 916 is a design choice based on the desired functionality of the plasma generator 900.

In various exemplary, non-limiting embodiments, the cavity 910 of the dielectric body 905 is hermetically sealed or closed, but for the gas inlet 920 and the discharge aperture 916.

At least one anode 934 is fitted or formed within or proximate the cavity 910 of the dielectric body 905 proximate the first end wall 912.

The anode 934 comprises an electrically conductive material, such as, for example, a metal, and may optionally include one or more anode apertures 932 formed therethrough. The anode 934 is electrically coupled, via an electrical connection 936, to a power supply 970. In various exemplary embodiments, the anode 934 comprises a plate. Alternatively, the anode 934 may comprise a mesh or mesh-like formation of material.

At least one cathode 944 is fitted or formed on the exterior side of the second end wall 914, so is to be isolated from the cavity 910. The cathode 944 is formed so as to at least partially encircle the discharge aperture 916.

The cathode 944 comprises an electrically conductive material, such as, for example, a metal. In various exemplary embodiments, the cathode 944 may be positioned on the exterior of the second end wall 914 or may be embedded within the second end wall 914. The cathode 944 is attached or coupled to the second end wall 914 such that at least a portion of the second end wall 914 isolates the cathode 944 from the cavity 910. Thus, any gas that flows through the cavity 910 is isolated from the cathode 944 such that the gas does not come into direct contact with the cathode 944, at least until the gas exits the discharge aperture 916.

The cathode 944 is electrically coupled, via an electrical connection 946, to the power supply 970.

Utilizing the plasma generator 900, a carrier gas (or mixture) is introduced proximate the first end wall 912 of the dielectric body 905, via the one or more gas inlet(s) 920. As the carrier gas (or mixture) is injected into the one or more gas inlet(s) 920, the gas flows through the cavity 910 of the dielectric body 905 and exits through the discharge aperture 916.

When power is applied to the anode 934 and the cathode 944, the injected gas breaks down and a plasma plume 980 is launched through the discharge aperture 916. The generated plasma plume 980 generally extends from the plasma generator 900 in a direction that is substantially parallel to the longitudinal axis of the plasma generator 900. The generated plasma plume 980 is at room temperature and remains stable so long as the carrier gas is flowing and an appropriate amount of power is applied to the anode 934 and the cathode 944, as further described herein.

Figure 10A:
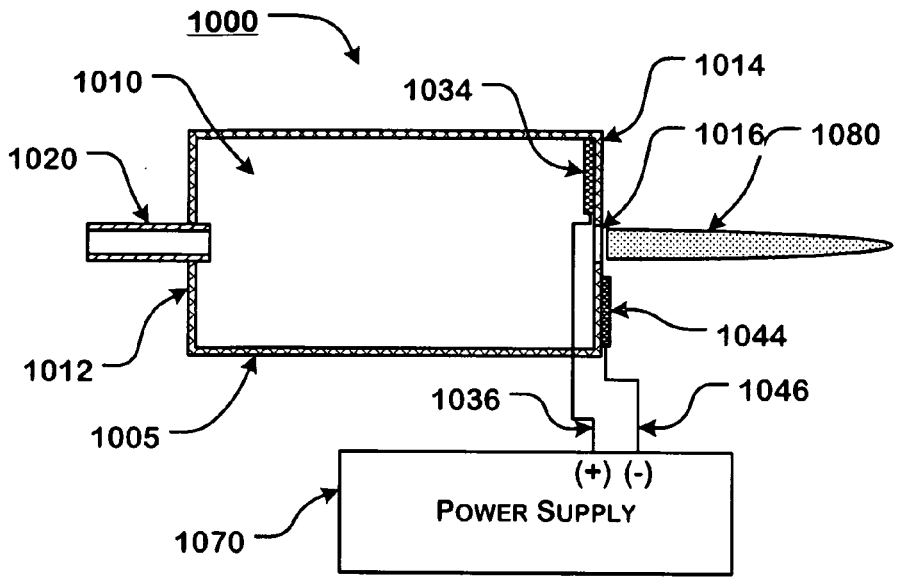
FIG. 10A shows a cross-sectional view of a tenth illustrative, non-limiting embodiment of an exemplary plasma generator according to this invention.
Figure 10B:
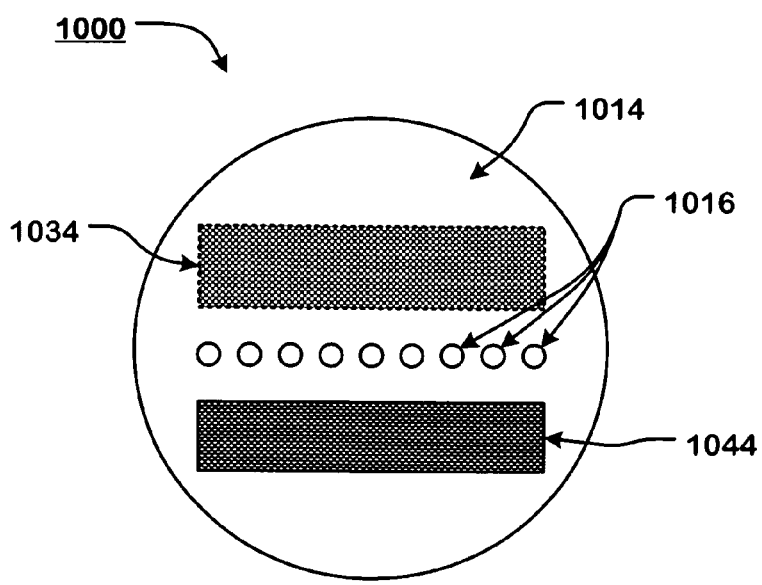
FIG. 10B shows a front view of the tenth illustrative, non-limiting embodiment of an exemplary plasma generator according to this invention.

FIGS. 10A and 10B show a cross-sectional view and a front view, respectively, of an tenth illustrative, non-limiting embodiment of an exemplary plasma generator according to this invention. As illustrated in FIGS. 10A and 10B, the plasma generator 1000 comprises a dielectric body 1005 having a first end wall 1012 and a second end wall 1014 and defining a cavity 1010.

One or more gas inlets 1020 is/are located proximate the first end wall 1012 of the dielectric body 1005 and is/are in fluid communication with the cavity 1010 of the plasma generator 1000, as further described herein.

A plurality of discharge apertures 1016 are formed through the second end wall 1014. In various exemplary embodiments, the discharge apertures 1016 are arranged in a particular pattern, such as, for example a line. It should be appreciated that the size, shape, and arrangement of the discharge apertures 1016 is a design choice based on the desired functionality of the plasma generator 1000.

In various exemplary, non-limiting embodiments, the cavity 1010 of the dielectric body 1005 is hermetically sealed or closed, but for the gas inlet(s) 1020 and the discharge apertures 1016.

At least one anode 1034 is fitted or formed within or proximate the cavity 1010 of the dielectric body 1005 proximate the second end wall 1014.

The anode 1034 comprises an electrically conductive material, such as, for example, a metal, and may optionally include one or more anode apertures formed therethrough. The anode 1034 is electrically coupled, via an electrical connection 1036, to a power supply 1070. In various exemplary embodiments, the anode 1034 comprises a strip or plate. Alternatively, the anode 1034 may comprise a mesh or mesh-like formation of material.

At least one cathode 1044 is fitted or formed on the exterior side of the second end wall 1014, so is to be isolated from the cavity 1010. The cathode 1044 is formed so as to at least partially encircle the discharge apertures 1016.

The cathode 1044 comprises an electrically conductive material, such as, for example, a metal. In various exemplary embodiments, the cathode 1044 may be positioned on the exterior of the second end wall 1014 or may be embedded within the second end wall 1014. The cathode 1044 is attached or coupled to the second end wall 1014 such that at least a portion of the second end wall 1014 isolates the cathode 1044 from the cavity 1010. Thus, any gas that flows through the cavity 1010 is isolated from the cathode 1044 such that the gas does not come into direct contact with the cathode 1044, at least until the gas exits the discharge apertures 1016.

The cathode 1044 is electrically coupled, via an electrical connection 1046, to the power supply 1070.

Utilizing the plasma generator 1000, a carrier gas (or mixture) is introduced proximate the first end wall 1012 of the dielectric body 1005, via the one or more gas inlet(s) 1020. As the carrier gas (or mixture) is injected into the one or more gas inlet(s) 1020, the gas flows through the cavity 1010 of the dielectric body 1005 and exits through the discharge apertures 1016.

When power is applied to the anode 1034 and the cathode 1044, the injected gas breaks down and a plasma plume 1080 is launched through each of the discharge apertures 1016. The generated plasma plumes 1080 generally extend from the plasma generator 1000 in a direction that is substantially parallel to the longitudinal axis of the plasma generator 1000. The generated plasma plumes 1080 are at room temperature and remains stable so long as the carrier gas is flowing and an appropriate amount of power is applied to the anode 1034 and the cathode 1044, as further described herein.

While this invention has been described in conjunction with the exemplary embodiments outlined above, it is evident that many alternatives, modifications, and variations will be apparent to those skilled in the art.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method for producing a plasma plume utilizing a plasma generator, the plasma generator, comprising:
   a dielectric body extending from a first end to a second end, wherein a cavity is defined within the dielectric body between the first end and the second end;
   at least one gas inlet formed proximate the first end of the dielectric body;
   at least one nozzle aperture formed proximate the second end of the dielectric body;
   at least one anode formed at least substantially around an outer surface of the dielectric body, wherein the anode is electrically coupled, via an electrical connection, to a power supply, and
   at least one cathode formed at least substantially around the outer surface of the dielectric body, wherein the cathode is spaced apart from the anode, wherein the cathode is located outside the cavity of the dielectric body, and wherein the cathode is electrically coupled, via an electrical connection, to the power supply, the method comprising:
   injecting a carrier gas into the gas inlet, wherein the carrier gas flows from the gas inlet to the nozzle aperture;
   applying a pulsed voltage applied at a regulated frequency to the anode, via the electrical connection, from the power supply;
   applying a pulsed voltage applied at a regulated frequency to the cathode, via the electrical connection, from the power supply; and
   producing a plasma plume, in atmospheric pressure, from the nozzle aperture.

2. The method of claim 1, wherein the carrier gas comprises helium, helium and oxygen, argon, nitrogen, air, or an equivalent.

3. The method of claim 1, wherein applying a pulsed voltage to the anode comprises applying a pulsed voltage with a magnitude from 2 kilovolts to 12 kilovolts.

4. The method of claim 1, wherein applying a pulsed voltage to the anode comprises applying a pulsed voltage at a pulse width of between 200 nanoseconds to 5 microseconds.

5. The method of claim 1, wherein applying a pulsed voltage to the anode comprises applying a pulsed voltage at a pulse width of 200 nanoseconds or less.

6. The method of claim 1, wherein applying a pulsed voltage to the anode comprises applying a pulsed voltage at a pulse width of 5 microseconds or more.

7. The method of claim 1, wherein applying a pulsed voltage to the anode comprises applying a pulsed voltage at a frequency of 1 kilohertz to 10 kilohertz or higher.

8. The method of claim 1, wherein applying a pulsed voltage to the anode comprises applying an alternating current voltage, a radio frequency power, or regulated voltage pulses.

9. The method of claim 1, further comprising using the plasma plume to aid in disinfecting wounds, healing wounds, coagulating blood, whitening teeth, disinfecting root canals, and/or removing plaque.

* * * * *

UNITED STATES PATENT AND TRADEMARK OFFICE
CERTIFICATE OF CORRECTION

PATENT NO.         : 8,460,283 B1
APPLICATION NO.    : 12/583222
DATED              : June 11, 2013
INVENTOR(S)        : Mounir Laroussi It is certified that error appears in the above-identified patent and that said Letters Patent is hereby corrected as shown below:

In the Specifications:

Column 4, Line 51, delete "cathode 144'" and insert --cathode 144--.

In the Claims:

Claim 1, under Column 14, Lines 1 and 2, delete "at least one cathode formed at least substantially around the outer surface of the dielectric body, wherein the cathode" and insert --at least one cathode formed at least substantially around an outer surface of the dielectric body, wherein the cathode--.

Signed and Sealed this
Sixteenth Day of July, 2013

Teresa Stanek Rea
*Acting Director of the United States Patent and Trademark Office*